Jan. 17, 1956 H. C. SWIM Plant Pat. 1,450
ROSE PLANT
Filed March 7, 1955
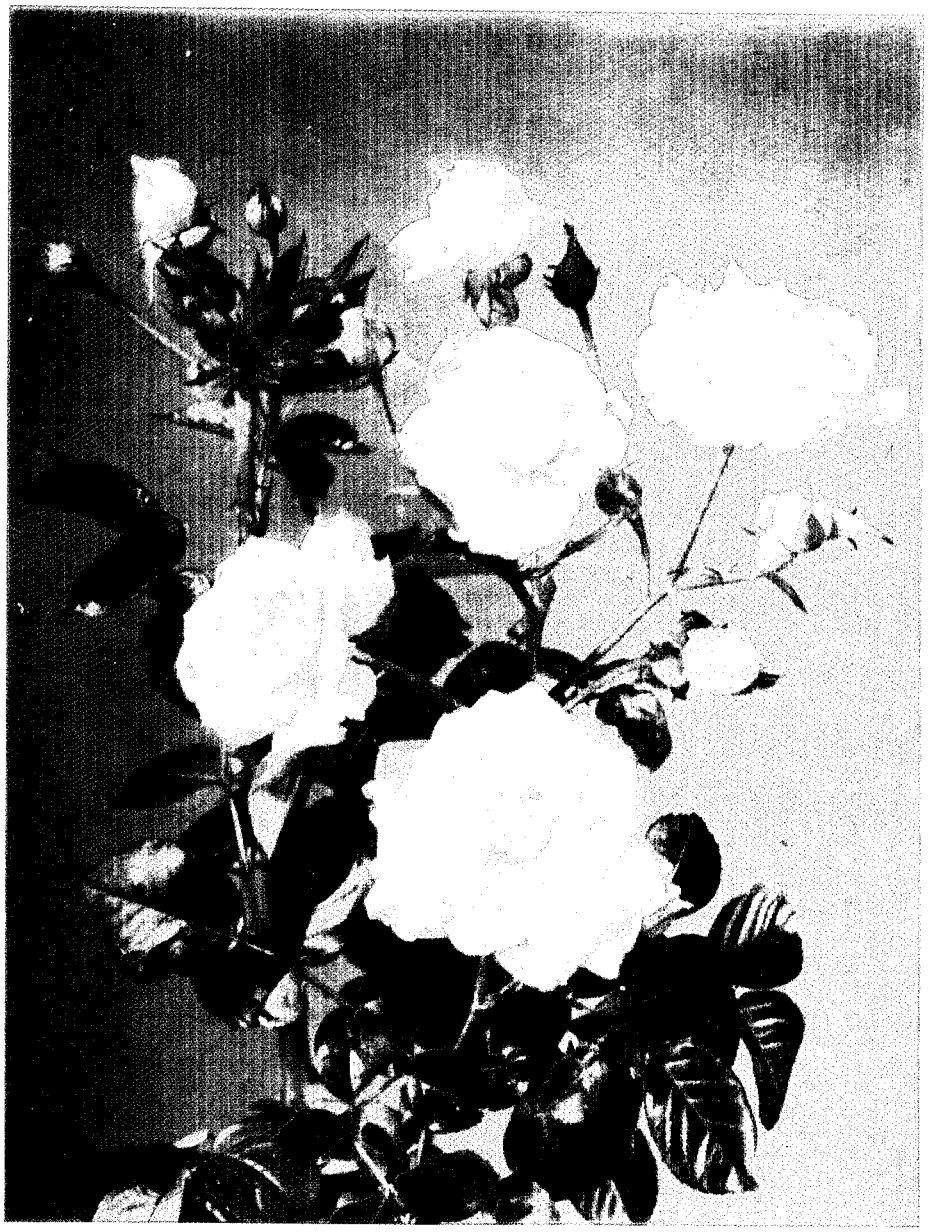
Inventor.
H. C. Swim
By: Robb & Robb
Attorneys.

United States Patent Office

Plant Pat. 1,450
Patented Jan. 17, 1956

1,450

ROSE PLANT

Herbert C. Swim, Ontario, Calif., assignor to Armstrong Nurseries, Inc., Ontario, Calif., a corporation of California Application March 7, 1955, Serial No. 492,817

1 Claim. (Cl. 47—61)

The present invention relates to a new and distinct variety of rose plant of the hybrid polyantha class from the standpoint of function, but of the hybrid tea class from the standpoint of heredity, which was originated by me by crossing the variety "Sutter's Gold" (Plant Patent No. 885) with the variety "Ondine" (unpatented).

The primary objective in making this cross was to produce a new rose variety which combines the most desirable characteristics of the two parent varieties. This objective was fully achieved, as evidenced by the fact that the combination of genes from both parents has produced a new variety having certain functional characteristics of the hybrid polyantha class, but which bears flowers of a size much larger than usual for varieties of this class, the size of the flowers of the new variety being comparable to those of the hybrid tea class.

In addition to the large size of the flowers, my new variety is characterized by the following outstanding features which, taken together, represent a unique and commercially desirable combination of characteristics:

(1) Very double blooms borne in clusters of several to the stem;

(2) Nearly white color around the outer portion of the flowers, with shades of yellow and orange toward the center of the flowers;

(3) Abundant production of blooms more or less continuously during the growing season; and (4) Abundant dark green, flat foliage which covers the plant well and enhances the overall attractiveness of the plant.

In comparison with its seed parent, "Sutter's Gold," which is classified in the hybrid tea class and is typical of that class, my new variety is functionally classified as a hybrid polyantha; the blooms of my new variety are very double, having from 60 to 100 petals, whereas the blooms of "Sutter's Gold" usually have from 30 to 35 petals; the blooms of the new variety are nearly white on their outer portions, with their inner portions shading in varying degrees of yellow, orange and sometimes light pink, whereas those of "Sutter's Gold" are golden yellow, with markings of pink or red particularly on the outer petals of the flowers; and the plant of my new variety is relatively low-growing as compared with that of "Sutter's Gold" which is tall-growing.

As compared with its pollen parent, "Ondine," which is classified in the hybrid tea class, my new variety is more properly classified functionally in the hybrid polyantha class; the many petals of the flowers of the new variety far exceed the semi-double flowers of "Ondine" which has from 20 to 25 petals; and the almost white color, with shading of yellow, orange and light pink in the blooms of my new variety is different from the creamy white, slightly pink-tinted blooms of "Ondine."

The foregoing characteristics and distinctions definitely differentiate my new variety from its parents, as well as from all other varieties of which I am aware.

Asexual reproduction of my new variety by budding at Ontario, California, shows that the aforementioned characteristics and distinctions come true to form and are established and transmitted through succeeding propagations.

The accompanying drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for garden decoration.

Class: Functionally hybrid polyantha, but hybrid tea in heredity.

Breeding: Seedling.

*Seed parent.*—"Sutter's Gold."

*Pollen parent.*—"Ondine."

Propagation: Holds its distinguishing characteristics through succeeding propagations by budding.

FLOWER

Locality where grown and observed: Ontario, California.

Flowers borne: Usually several to stem; in regular, rounded cluster; on medium length stems of normal strength.

Quantity of bloom: Abundant, outdoors.

Continuity: Nearly continuous during growing season.

Fragrance: Penetrating. Nature—tea.

Bud:

*Peduncle.*—From average length to long; average caliper; erect; moderately smooth; some gland-tipped cilia. Color—between Courge Green, Plate XVII (Ridgway) and Biscay Green, Plate XVII (Ridgway), overlaid with near Indian Red, Plate XXVII (Ridgway) on side exposed to the sun.

*Before calyx breaks.*—Size—medium. Form—from short to medium length; ovoid; with foliaceous appendages and some tomentum; few gland-tipped cilia on the surface of the bud; usually without much-cut foliaceous parts extending beyond the tip of the bud.

*As calyx breaks.*—Color—between Uranium Green, Plate 63/2, page 63 (Wilson) and Dresden Yellow, Plate 64/3, page 64 (Wilson), marked somewhat with between Geranium Lake, Plate 20/1, page 20 (Wilson) and Carmine, Plate 21/3, page 21 (Wilson), and sometimes near white, with small area near base equal to approximately ⅙ of petal surface between Sap Green, Plate 62/2, page 62 (Wilson) and Uranium Green, Plate 63/2, page 63 (Wilson).

*Sepals.*—Inner surface with fine woolly tomentum; margins of alternate sepals lined with fine woolly tomentum; others lined with gland-tipped cilia and hairs.

*As first petal opens.*—Size—average. Form—medium length; from ovoid to somewhat globular. Color: Outside—between white and Primrose Yellow, Plate 601/3, page 65 (Wilson), with markings of between Geranium Lake, Plate 20/2, page 20 (Wilson) and Carmine, Plate 21/2, page 21 (Wilson) particularly along margins of petal; area at base of petal near attachment between Empire Yellow, Plate 603/1, page 66 (Wilson) and Empire Yellow, Plate 603, page 66 (Wilson), but sometimes marked with near Carmine, Plate 21/3, page 21 (Wilson). Inside—between Empire Yellow, Plate 603/3, page 66 (Wilson) and Empire Yellow, Plate 603/2, page 66 (Wilson), shading into near Empire Yellow, Plate 603, page 66 (Wilson) toward base of petal; very lightly marked with near Geranium Lake, Plate 20/3, page 20 (Wilson), particularly near margins of petal.

*Opening.*—Opens up well; is not retarded from opening by cold, hot, wet or dry weather.

Bloom:

*Size (when fully open).*—Large for class; from 2¾ to 3½ inches.

*Petalage.*—Very double; from 60 to 100 petals, plus 20 to 30 petaloids; arranged regularly.

*Form.*—Somewhat globular at first, but becoming open to cupped later; petals at first being cupped, with lateral margins usually reflexed slightly from ⅙ to ⅓ of upper portion of the petal, and with apex sometimes reflexed ⅓ or more of petal length particularly on outer petals; becoming later at maturity flat-cupped, with lateral margins sometimes reflexed from ⅓ to ¾ of petal length, and with apex sometimes reflexed ⅓ or more of petal length.

Petals:

*Texture.*—Thin; moderately soft; with inside satiny and outside from shiny to satiny.

*Shape.*—Outside—Broadly obovate, with apex flat and occasionally with 1 or 2 notches. Intermediate—obovate, with apex from rounded to flat and occasionally with 1 or 2 notches. Inside—narrowly obovate; irregular; with apex rounded and sometimes with 1 or 2 notches.

This description of a newly opened flower was made from a rose grown outdoors in the month of October, at Ontario, California:

*Color.*—Outside petal: Outside surface—near white, with portions of petal sometimes shaded very lightly with near Primrose Yellow, Plate 601/3, page 65 (Wilson), and with markings of near Crimson, Plate 22/3, page 22 (Wilson); small area at base of petal near attachment near Empire Yellow, Plate 603, page 66 (Wilson). Inside surface—near white, with only very slight shading of near Crimson, Plate 22/3, page 22 (Wilson) particularly around margins of the petal; small area at base of petal near attachment near Empire Yellow, plate 603, page 66 (Wilson). Intermediate petal: Outside surface—near Empire Yellow, Plate 603/1, page 66 (Wilson), marked particularly around margins with near Geranium Lake, Plate 20/2, page 20 (Wilson); small area at base of petal near attachment near Empire Yellow, Plate 603, page 66 (Wilson). Inside surface—near Empire Yellow, Plate 603/1, page 66 (Wilson), shading into near Empire Yellow, Plate 603, page 66 (Wilson) toward base of the petal; sometimes shading only very lightly around margins with near Geranium Lake, Plate 20/3, page 20 (Wilson). Inner petal: Outside surface—near Empire Yellow, Plate 603/1, page 66 (Wilson), marked particularly around margins and upper portion of petal with near Geranium Lake, Plate 20/2, page 20 (Wilson); small area at base of petal near attachment near Empire Yellow, Plate 603, page 66 (Wilson). Inside surface—near Empire Yellow, Plate 603, page 66 (Wilson), sometimes very lightly shaded with near Geranium Lake, Plate 20/3, page 20 (Wilson).

This description was made from a rose that was open for 3 days outdoors in the month of October, at Ontario, California:

*Color.*—Outside petal: Outside surface—near white, but sometimes very lightly shaded with near Rose Madder, Plate 23/3, page 23 (Wilson); very small area at base of petal near attachment near Empire Yellow, Plate 603, page 66 (Wilson). Inside surface—near white, with small area at base of petal near attachment near Empire Yellow, Plate 603, page 66 (Wilson). Inside petal: Outside surface—near white, but sometimes shaded with near Empire Yellow, Plate 603/3, page 66 (Wilson), and sometimes lightly shaded around margins with near Carmine, Plate 21/3, page 21 (Wilson); small area at base of petal near attachment near Empire Yellow, Plate 603, page 66 (Wilson). Inside surface—near white, but sometimes shaded with near Empire Yellow, Plate 603/2, page 66 (Wilson); small area at base of petal near attachment near Empire Yellow, Plate 603, page 66 (Wilson).

*General color effect.*—Newly opened flower—outer portion of bloom near white, but sometimes very lightly marked with near Crimson, Plate 22/3, page 22 (Wilson); inner portion of bloom near Empire Yellow, Plate 603/1, page 66 (Wilson), but often overlaid or shaded with near Geranium Lake, Plate 20/2, page 20 (Wilson). 3-days open—outer portion of bloom near white, but sometimes marked very lightly with near Rose Madder, Plate 23/3, page 23 (Wilson); inner portion of bloom near white, but sometimes overlaid or shaded with near Empire Yellow, Plate 603/1, page 66 (Wilson), and sometimes shaded with near Carmine, Plate 21/3, page 21 (Wilson).

*Behavior.*—Usually drop off cleanly except for petaloids; yellow shading of bloom becomes more pronounced in cool weather and bloom becomes lighter in color in warm weather.

*Flower longevity.*—On bush in garden—4 or 5 days in November. Cut roses grown outdoors and kept at livingroom temperatures—5 days in November.

REPRODUCTIVE ORGANS

Stamens: Few; arranged irregularly about pistils; mixed with petaloids.

Filaments: Short; from 2 to 4 mm. in length; most with anthers.

*Color.*—Between Uranium Green, Plate 63/3, page 63 (Wilson) and Dresden Yellow, Plate 64/3, page 64 (Wilson).

Anthers: Medium size; all open approximately at once.

*Color.*—Upper side—margins between Indian Yellow, Plate 6/1, page 6 (Wilson) and Saffron Yellow, Plate 7/2, page 7 (Wilson); remainder near Aureolin, Plate 3/3, page 3 (Wilson). Under surface—margins between Indian Yellow, Plate 6/1, page 6 (Wilson) and Saffron Yellow, Plate 7/2, page 7 (Wilson); remainder near Aureolin, Plate 3/3, page 3 (Wilson).

Pollen: Sparse.

*Color.*—Near Indian Yellow, Plate 6/2, page 6 (Wilson).

Pistils: Few; approximately 35 in number.

Styles: Moderately even; average length; from 7 to 10 mm. in length; average caliper; loosely bunched.

*Color.*—Lower one-half of style near Uranium Green, Plate 63/3, page 63 (Wilson); upper one-half of style near Currant Red, Plate 821/3, page 167 (Wilson).

Stigma:

*Color.*—Near Lemon Yellow, Plate 4/3, page 4 (Wilson).

Ovaries: Most enclosed in calyx, with few protruding from calyx.

Hips: None.

Sepals: Permanent; medium length; recurved.

*Color.*—Inside—between Biscay Green, Plate XVII (Ridgway) and Bice Green, Plate XVII (Ridgway);

sometimes marked with near Indian Red, Plate XXVII (Ridgway); masked by white woolly tomentum. Outside—between Light Elm Green, Plate XVII (Ridgway) and Bice Green, Plate Plate XVII (Ridgeway); sometimes marked with near Indian Red, Plate XXVII (Ridgway).

Seeds: None.

PLANT

Foliage:

*Leaves.*—Compound of usually 5 to 7 leaflets; abundant; medium size; leathery; semi-glossy.

*Leaflets.*—Shape—ovoid, with acute apex. Base—round. Margin—simply serrate.

*Color.*—Mature: Upper surface—between Forest Green, Plate XVII (Ridgway) and Deep Dull Yellow Green (1), Plate XXXII (Ridgeway). Under surface—between Light Bice Green, Plate XVII (Ridgway) and Chromium Green, Plate XXXII (Ridgway). Young: Upper surface—near Bice Green, Plate XVII (Ridgway), overlaid particularly along margins with near Dark Corinthian Purple, Plate XXXVIII (Ridgeway). Under surface—near Chromium Green, Plate XXXII (Ridgway), heavily overlaid with near Corinthian Purple, Plate XXXVII (Ridgway).

*Rachis (the supporting stem of the compound leaf).*—Average size. Upper side—Grooved; hairy; some stipitate glands on edges. Under side—moderately prickly (3 to 5 prickles); with stipitate glands.

*Stipules.*—Long; narrow; with medium length points turning out at an angle of more than 45°; recurved toward the stem.

*Disease resistance.*—Average resistance to mildew as compared with other varieties grown under comparable cultural conditions at Ontario, California.

Growth:

*Habit.*—Bushy; somewhat spreading; much-branched.

*Growth.*—Free.

*Canes.*—Medium caliper.

*Main stems.*—Color—between Oil Green, Plate V (Ridgway) and Spinach Green, Plate V (Ridgway).

Large prickles—many; long; almost straight; with long, narrow base. Color—between Light Drab, Plate XLVI (Ridgway) and Light Grayish Olive, Plate XLVI (Ridgeway). Small prickles—from few to several. Color—between Light Drab, Plate XLVI (Ridgway) and Light Grayish Olive, Plate XLVI (Ridgway). Hairs—none.

*Branches.*—Color—near Bice Green, Plate XVII (Ridgway). Large prickles—many; long; almost straight; with moderately long, narrow base. Color—between Verona Brown, Plate XXIX (Ridgway) and Snuff Brown, Plate XXIX (Ridgway). Small prickles—from few to several. Color—between Verona Brown, Plate XXIX (Ridgway) and Snuff Brown, Plate XXIX (Ridgway). Hairs—None.

*New shoots.*—Color—between Biscay Green, Plate XVII (Ridgway) and Light Bice Green, Plate XVII (Ridgway), overlaid with between Corinthian Purple, Plate XXXVIII (Ridgway) and Neutral Red, Plate XXXVIII (Ridgway). Large prickles—several; medium length· almost straight; with moderately long, narrow base. Color—near Corinthian Purple, Plate XXXVIII (Ridgway). Small prickles—several. Color—near Corinthian Purple, Plate XXXVIII (Ridgway). Hairs—none.

I claim:

A new and distinct variety of rose plant of the hybrid polyantha class from a functional standpoint but of the hybrid tea class from a heredity standpoint, substantially as herein shown and described, characterized particularly as to novelty by its abundant, relatively flat, dark green foliage which covers the plant well, its abundant production of blooms substantially continuously during the growing season, the relatively large size, very double form and cluster habit of its blooms, and the distinctive color of the blooms, said color being nearly white around the outer portion of the flower and being shaded in varying shades of yellow, orange and sometimes light pink at the inner portion of the flower.

No references cited.